United States Patent

Ueno et al.

[11] Patent Number: 5,914,399
[45] Date of Patent: Jun. 22, 1999

[54] METHOD FOR PRODUCING 5-ISOPROPYLURACIL

[75] Inventors: Hiroki Ueno; Michio Matsuda; Susumu Nishizawa, all of Osaka, Japan

[73] Assignee: Sumika Fine Chemicals Co., Ltd., Osaka, Japan

[21] Appl. No.: 09/175,686

[22] Filed: Oct. 20, 1998

[30] Foreign Application Priority Data

Oct. 22, 1997 [JP] Japan .................................. 9-290161
Sep. 16, 1998 [JP] Japan ................................ 10-261942

[51] Int. Cl.$^6$ .................................................. C07D 239/54
[52] U.S. Cl. .............................................................. 544/309
[58] Field of Search .............................................. 544/309

[56] References Cited

U.S. PATENT DOCUMENTS

| | | | |
|---|---|---|---|
| 2,098,954 | 11/1937 | Dalmer et al. | 544/309 |
| 2,259,925 | 10/1941 | Dalmer et al. | 544/309 |
| 2,413,303 | 6/1946 | Curd | 544/309 |
| 3,149,106 | 9/1964 | Loers | 544/309 |
| 3,324,127 | 6/1967 | Rafos et al. | 544/309 |
| 3,330,640 | 7/1967 | Luckenbaugh | 544/309 |
| 3,560,504 | 2/1971 | Gauri et al. | 544/309 |

FOREIGN PATENT DOCUMENTS

| | | |
|---|---|---|
| 61-12906 | 4/1986 | Japan . |
| 7-17953 | 1/1995 | Japan . |

OTHER PUBLICATIONS

*Chemical Abstracts*, 20, 1216 (1925).
*Chemical Abstracts*, 70, 87733h (1969).

*Primary Examiner*—John M. Ford
*Attorney, Agent, or Firm*—Leydig, Voit & Mayer, Ltd.

[57] ABSTRACT

A method for producing 5-isopropyluracil at a high yield in a short time, wherein N-(2-cyano-3-methylbutanoyl)urea is reduced in a 10–15% aqueous sulfuric acid solution in the presence of palladium carbon at 30–45° C., heated for ring closure reaction and added to a 50–70% aqueous sulfuric acid solution to give 5-isopropyluracil having a high purity.

5 Claims, No Drawings ically preferably at 35–45° C. When

METHOD FOR PRODUCING 5-ISOPROPYLURACIL

TECHNICAL FIELD OF THE INVENTION

The present invention relates to a method for producing 5-isopropyluracil. More particularly, the present invention relates to a method for producing 5-isopropyluracil useful as a synthetic intermediate for pharmaceutical products such as anti-HIV drugs and antiviral drugs.

BACKGROUND OF THE INVENTION

The objective compound of the present invention, 5-isopropyluracil, is useful as a synthetic intermediate for pharmaceutical products such as anti-HIV drugs and antiviral drugs. The method for producing 5-isopropyluracil is disclosed in Japanese Patent Unexamined Publication No. 17953/1995, wherein conc. hydrochloric acid, conc. sulfuric acid and the like are added to N-(2-cyano-3-methylbutanoyl)urea for reduction and the resulting reaction mixture is heated at 80–100° C.

According to this method, 5-isopropyluracil can be obtained at a comparatively high yield without generating a bad odor. However, production of 5-isopropyluracil at a high yield requires 10 hours or more of reduction and use of a large amount of catalyst. Thus, there remains a demand for a method for producing highly pure 5-isopropyluracil on an industrial scale at a high yield in a short time.

It is therefore an object of the present invention to provide a method for producing highly pure 5-isopropyluracil at a high yield in a short time.

SUMMARY OF THE INVENTION

According to the present invention, there has now been provided a method for producing 5-isopropyluracil at a high yield in a short time, which comprises reducing N-(2-cyano-3-methylbutanoyl)urea in a 10–15% aqueous sulfuric acid solution in the presence of palladium carbon and heating the resulting mixture for ring closure reaction. In particular, reduction at 30–45° C. has been found to produce 5-isopropyluracil at a high yield in a short time. In addition, when the reaction mixture resulting from the ring closure reaction was added to a 50–70% aqueous sulfuric acid solution, 5-isopropyluracil could be separated at a high yield in a short time.

That is, the present invention provides the following.

(1) A method for producing 5-isopropyluracil, which comprises reducing N-(2-cyano-3-methylbutanoyl) urea in a 10–15% aqueous sulfuric acid solution in the presence of palladium carbon.

(2) The production method of (1) above, wherein the reduction is carried out at 30–45° C.

(3) The production method of (1) above, wherein the reduction is carried out at 30–40° C.

(4) The production method of (1) above, wherein the reduction is carried out at 35–45° C.

(5) The production method of (1) above, wherein the reaction mixture after reduction is heated and added to a 50–70% aqueous sulfuric acid solution to allow precipitation of 5-isopropyluracil.

DETAILED DESCRIPTION OF THE INVENTION

In the present invention, the concentration (%) of the aqueous sulfuric acid solution is in w/w%.

5-Isopropyluracil can be produced at a high yield in a short time by reducing N-(2-cyano-3-methylbutanoyl)urea in an aqueous sulfuric acid solution having a specific concentration in the presence of palladium carbon and heating the resulting mixture for ring closure reaction, thereby allowing precipitation of 5-isopropyluracil. In particular, reduction in a specific temperature range enables production of 5-isopropyluracil at a high yield in a short time.

In the present invention, palladium carbon is used as a catalyst. Palladium carbon is advantageous over Raney catalysts represented by Raney nickel, in that it can quickly accelerate the reaction.

Palladium carbon is used in an amount that enables sufficient manifestation of the effect usually achieved by the use thereof—reaction rate accelerating effect. For example, when 10% palladium carbon (50% wet product) is used, the amount thereof is not less than 0.2 part by weight, preferably not less than 1 part by weight, per 100 parts by weight of N-(2-cyano-3-methylbutanoyl)urea. In consideration of economical aspects and a shorter time desirable for removing the catalyst, the amount thereof is preferably not more than 10 parts by weight, more preferably not more than 5 parts by weight.

The aqueous sulfuric acid solution to be used in the present invention for reduction is required to have a concentration of 10–15%. When an aqueous sulfuric acid solution having the specific concentration mentioned above is used at the below-mentioned reduction temperature, N-(2-cyano-3-methylbutanoyl)urea can be reduced quickly while inhibiting foaming during reaction. When the aqueous sulfuric acid solution has a concentration of less than 10%, the reaction proceeds slowly, and when it exceeds 15%, the reaction becomes slow again, since partial N-(2-cyano-3-methylbutanoyl)urea proceeds to ring closure during the reduction and the resulting 5-isopropyluracil crystals cover the catalyst.

The 10–15% aqueous sulfuric acid solution is used in an amount of 200–1000 parts by weight, preferably 500–800 parts by weight, per 100 parts by weight of N-(2-cyano-3-methylbutanoyl)urea.

The reduction in the present invention is carried out preferably at 30–45° C., more preferably at 30–40° C. or at 35–45° C., and particularly preferably at 35–45° C. When the temperature of reduction is less than 30° C., reduction proceeds slowly and when it exceeds 45° C., 5-isopropyluracil resulting from part of N-(2-cyano-3-methylbutanoyl)urea slows the reduction, thereby causing excessive reduction that makes separation of the objective compound difficult. This is because higher temperatures slow absorption of hydrogen, as a result of which the reaction takes time, often resulting in excessive reduction.

In the present invention, reduction is carried out upon displacement of the inside of the reaction vessel with hydrogen gas. For this end, the pressure of the hydrogen gas is set from normal pressure to 5 kg/cm$^2$, preferably 0.2–1 kg/cm$^2$ or 0.5–3 kg/cm$^2$. Reduction can be also carried out by bubbling hydrogen gas through an aqueous sulfuric acid solution while stirring the solution. The termination of the reduction can be confirmed by the completion of hydrogen absorption.

When the reaction temperature is raised as mentioned above, absorption of hydrogen gas becomes slow, and the hydrogen gas pressure needs to be increased. By increasing the hydrogen gas pressure along with the reaction temperature, the absorption of hydrogen gas is accelerated and the reaction ends in a short time. Consequently, side products are not produced and a highly pure objective compound can be obtained at a high yield. When the reaction temperature is set to 30–40° C., the hydrogen gas pressure is preferably 0.2–1 kg/cm$^2$ and when the reaction temperature is set to 35–45° C., the hydrogen gas pressure is preferably 0.5–3 kg/cm, with particular preference given to the reaction temperature of 35–45° C. and the hydrogen gas pressure of 0.5–3 kg/cm$^2$, whereby the reaction time can be shortened.

The ring closure reaction in the present invention is accomplished by heating the reaction mixture upon confirmation of the termination of the reduction. The heating temperature for ring closure is 80–100° C., preferably 85–90° C. and the heating time is 1–10 hours, preferably 3–6 hours.

In the present invention, 5-isopropyluracil can be isolated by, for example, neutralizing the obtained reaction mixture with an aqueous alkali solution of sodium hydroxide, potassium hydroxide and the like to dissolve the objective compound, and filtering off the catalyst. The obtained filtrate is added to an aqueous sulfuric acid solution having a given concentration to allow precipitation of the objective compound. The precipitate is collected by filtration, washed and dried to give 5-isopropyluracil. In this way, 5-isopropyluracil can be isolated in a short time.

The aqueous sulfuric acid solution to be used for the treatment in the present invention has a concentration of not less than 50%, preferably not less than 55%, from the viewpoint of volume efficiency, and not more than 70%, preferably not more than 65%, from the viewpoint of exothermic neutralition. The reaction mixture is added to the aqueous sulfuric acid solution having the above-mentioned specific concentration to yield bigger crystals that take only shortened time for filtration. When an aqueous acid solution is added to the reaction mixture, the crystals become smaller and the time necessary for filtration becomes longer. The amount used of the aqueous sulfuric acid solution having the above-mentioned specific concentration depends on the amount of alkali to be added to the reaction mixture. For example, when 450–550 parts by weight of a 25% aqueous sodium hydroxide solution is added to 100 parts by weight of N-(2-cyano-3-methylbutanoyl)urea, a 60% aqueous sulfuric acid solution is generally used in an amount of 150–400 parts by weight, preferably 200–350 parts by weight.

The starting compound, N-(2-cyano-3-methylbutanoyl) urea, is a known compound and can be obtained by, for example, reacting methyl cyanoacetate and acetone, hydrolyzing the resulting methyl 2-cyano-3-methylbutyrate with an aqueous sodium hydroxide solution, treating said reaction mixture with sulfuric acid to give 2-cyano-3-methylbutyric acid and heating this compound in the presence of urea and acetic anhydride.

5-Isopropyluracil obtained by the present invention can be suitably used as an intermediate for producing a medicament and the like.

The present invention is explained in more detail in the following by way of Examples, to which the present invention is not limited.

PRODUCTION EXAMPLE 1

Production of methyl 2-cyano-3-methylbutyrate

Methyl cyanoacetate (300 g, 3.028 moles), acetone (195 g, 3.36 moles), acetic acid (36.4 g), ammonium acetate (23.3 g) and 10% palladium carbon (50% wet product, 10.6 g) were added to methanol (480 g), and the mixture was reduced at 15–35° C. under a hydrogen gas pressure of 0.2–0.5 kg/cm$^2$. Upon confirmation of the completion of hydrogen absorption, 10% palladium carbon was filtered off from the reaction mire and methanol was evaporated from the filtrate. The obtained residue was analyzed by gas chromatography, whereby it was confirmed that methyl 2-cyano-3-methylbutyrate having a purity of 99.2% was obtained. The obtained compound was confirmed to be methyl 2-cyano-3-methylbutyrate by $^1$H-NMR.

$^1$H-NMR (250 MHz, DMSO-d$_6$)δ: 0.96, 1.04 (d, J=6.6 Hz, 6H, 2×CH$_3$), 2.31 (m, 1H, CH), 3.75 (s, 3H, CH$_3$), 4.18 (d, J=4.6 Hz, 1H, CH)

PRODUCTION EXAMPLE 2

Production of 2-cyano-3-methylbutyric acid

A solution of sodium hydroxide (183 g, 4.58 moles) in water (275 g) was added dropwise at 30° C. to methyl 2-cyano-3-methylbutyrate obtained in Production Example 1 (entire amount), and 30 minutes later, the mire was analyzed by liquid chromatography. As a result, the residual amount of the starting compound, methyl 2-cyano-3-methylbutyrate, was 0.1%.

To this reaction mixture was added dropwise a 78% aqueous sulfuric acid solution (290 g) at 25–35° C., and the reaction mixture was adjusted to pH 2. Anhydrous sodium sulfate (53 g) was further added and the mixture was stirred for 1 hour. The precipitated sodium sulfate was filtered off. Methanol was evaporated from this reaction mixture under reduced pressure and 2-cyano-3-methylbutyric acid in the residue was analyzed by liquid chromatography. As a result, it was confirmed that 2-cyano-3-methylbutyric acid had a purity of 87%. The obtained compound was confirmed to be 2-cyano-3-methylbutyric acid by $^1$H-NMR.

$^1$H-NMR (250 MHz, DMSO-d$_6$)δ: 1.2, 1.13 (d, J=6.6 Hz, 6H, 2×CH$_3$), 2.45 (m, 1H, CH), 4.13 (d, J=4.62 Hz, 1H, CH), 7.3 (br, 1H, COOH)

PRODUCTION EXAMPLE 3

Production of N-(2-cyano-3-methylbutanoyl)urea

Urea (218 g, 3.63 moles) and acetic anhydride (473 g, 4.63 moles) were added to 2-cyano-3-methylbutyric acid (385 g, 3.03 moles) obtained in Production Example 2. The reaction mixture was heated for 2 hours at 80–90° C. and hot water (80–90° C., 1926 g) was added dropwise to the reaction mixture.

This reaction mixture was cooled to room temperature (ca 25° C.) to allow precipitation of crystals. The obtained crystals were collected by filtration, washed with water and dried to give 455.9 g of N-(2-cyano-3-methylbutanoyl)urea (yield 89%). The obtained compound was confirmed to be N-(2-cyano-3-methylbutanoyl)urea by $^1$H-NMR.

$^1$H-NMR (250 MHz, DMSO-d$_6$)δ: 0.81, 0.85 (d, J=6.6 Hz, 6H, 2×CH$_3$), 2.12 (m, 1H, CH), 3.69 (d, J=4.6 Hz, 1H, CH), 7.3 (br, 2H, NH$_2$), 10.3 (br, 1H, NH)

EXAMPLE 1

To a 12% aqueous sulfuric acid solution (878 g) were added N-(2-cyano-3-methylbutanoyl)urea (140 g) and 10% palladium carbon (50% wet product, 7 g, amount used per 100 parts by weight of N-(2-cyano-3-methylbutanoyl)urea: 5 parts by weight) to carry out reduction at 30–35° C. under a hydrogen gas pressure of 0.2–0.5 kg/cm$^2$.

The absorption of hydrogen completed in 7 hours. The reaction mixture was heated at 85–90° C. for 4 hours, and a solution of sodium hydroxide (170 g) in water (250 g) was added to the reaction mixture at 15–30° C., and the catalyst was filtered off. The filtrate was added dropwise to a 60% aqueous sulfuric acid solution (330 g) at 20–30° C. to allow precipitation of the objective compound. The reaction mixture was filtered through a Nutsche funnel (time necessary for filtration: 14 minutes), and the obtained crystals were washed with water and dried to give 114.8 g of 5-isopropyluracil (yield 90%, purity 99.89%, melting point 287° C.).

The obtained compound was confirmed to be 5-isopropyluracil from the following physical property.

Elemental analysis: Found (%): C54.7, H6.8, N18.4; Calculated (%): C54.5, H6.5, N18.2; IR (KBr) cm$^{-1}$: 3080, 2960, 1730, 1668, 1246, 850

EXAMPLE 2

To a 14% aqueous sulfuric acid solution (889 g) were added N-(2-cyano-3-methylbutanoyl)urea (150 g) and 10% palladium carbon (50% wet product, 7.5 g, amount used per 100 parts by weight of N-(2-cyano-3-methylbutanoyl)urea: 5 parts by weight) to carry out reduction at 30–35° C. under a hydrogen gas pressure of 0.2–0.4 kg/cm$^2$.

The absorption of hydrogen completed in 8 hours. The reaction mixture was heated at 85–88° C. for 4 hours, a solution of sodium hydroxide (175 g) in water (255 g) was added to the reaction mixture at 15–30° C., and the catalyst was filtered off. The filtrate was added dropwise to a 60% aqueous sulfuric acid solution (335 g) at 20–30° C. to allow precipitation of the objective compound. The reaction mixture was filtered through a Nutsche funnel (time necessary for filtration: 14 minutes), and the obtained crystals were washed with water and dried to give 133 g of 5-isopropyluracil (yield 97.3%, purity 100%, melting point 287° C.).

Various spectrum data of the obtained 5-isopropyluracil were the same as those obtained in Example 1.

EXAMPLE 3

To a 12% aqueous sulfuric acid solution (720 g) were added N-(2-cyano-3-methylbutanoyl)urea (114 g) and 10% palladium carbon (50% wet product, 5.7 g, amount used per 100 parts by weight of N-(2-cyano-3-methylbutanoyl)urea: 5 parts by weight) to carry out reduction at 40–45° C. under a hydrogen gas pressure of 2.6–3.0 kg/cm$^2$.

The absorption of hydrogen completed in 2.5 hours. The reaction mixture was heated at 85–90° C. for 4 hours, a solution of sodium hydroxide (138 g) in water (412 g) was added to the reaction mixture at 20–30° C., and the catalyst was filtered off. The filtrate was added dropwise to a 60% aqueous sulfuric acid solution (345 g) at 90–95° C. to allow precipitation of the objective compound. The reaction mixture was cooled to 40° C. and filtered through a Nutsche funnel (time necessary for filtration: 18 minutes). The obtained crystals were washed with water and dried to give 94 g of 5-isopropyluracil (yield 90%, purity 99.8%, melting point 287° C.).

Various spectrum data of the obtained 5-isopropyluracil were the same as those obtained in Example 1.

COMPARATIVE EXAMPLE 1

In the same manner as in Example 1 except that 6% aqueous sulfuric acid solution (824 g) was used instead of the 12% aqueous sulfuric acid solution (878 g), reduction was carried out. The rate of hydrogen absorption became slow during the reaction, so that 10% palladium carbon (50% wet product, 14 g, amount used per 100 parts by weight of N-(2-cyano-3-methylbutanoyl)urea: 10 parts by weight) was further added to the reaction mixture. As a result, it took 13 hours to complete the hydrogen absorption.

The reaction mixture was treated in the same manner as in Example 1 to give 106 g of 5-isopropyluracil yield : 83.1%, purity : 99.75%).

COMPARATIVE EXAMPLE 2

In the same manner as in Example 1 except that a 20% aqueous sulfuric acid solution (970 g) was used instead of the 12% aqueous sulfuric acid solution (878 g) and 10% palladium carbon (50% wet product, 14 g, amount used per 100 parts by weight of N-(2-cyano-3-methylbutanoyl)urea: 10 parts by weight) was added instead of the 10% palladium carbon (50% wet product, 7 g), reduction was carried out. It took 21 hours to complete the hydrogen absorption.

The reaction mixture was treated in the same manner as in Example 1 to give 102 g of 5-isopropyluracil (yield: 80.0%, purity : 99.5%).

COMPARATIVE EXAMPLE 3

In the same manner as in Example 1 except that 14 g of 10% palladium carbon (50% wet product, amount used per 100 parts by weight of (N-(2-cyano-3-methylbutanoyl)urea: 10 parts by weight) was used and the temperature of reduction was changed from 30–35° C. to 40–45° C., reduction was carried out. The hydrogen absorption stopped during the reaction, so that 10% palladium carbon (50% wet product, 7 g, amount used per 100 parts by weight of N-(2-cyano-3-methylbutanoyl)urea: 5 parts by weight) was further added to the reaction mixture. As a result, it took 20 hours to complete the hydrogen absorption.

The reaction mixture was treated in the same manner as in Example 1 to give 109 g of 5-isopropyluracil (yield: 85.4%, purity: 99.74%).

comparative example 4

To a 12% aqueous sulfuric acid solution (878 g) were added N-(2-cyano-3-methylbutanoyl)urea (140 g) and 10% palladium carbon (50% wet product, 14 g, amount used per 100 parts by weight of N-(2-cyano-3-methylbutanoyl)urea: 10 parts by weight) to carry out reduction at 20–25° C. under a hydrogen gas pressure of 0.2–0.4 kg/cm$^2$. The reaction stopped halfway, so that 10% palladium carbon (50% wet product, 14 g, amount used per 100 parts by weight of N-(2-cyano-3-methylbutanoyl)urea: 10 parts by weight) was further added to the reaction mixture. As a result, it took 20 hours to complete the hydrogen absorption.

The reaction mixture was treated in the same manner as in Example 1 to give 92.9 g of 5-isopropyluracil (yield: 72.8%, purity: 98.4%).

COMPARATIVE EXAMPLE 5

To 4.7% hydrochloric acid (600 ml) were added N-(2-cyano-3-methylbutanoyl)urea (100 g) and 10% palladium carbon (50% wet product, 5 g) to carry out reduction at 20–30° C. under normal pressure and a hydrogen gas atmosphere. The reaction stopped halfway, so that 10% palladium carbon (50% wet product) was added 4 times (5 g at a time, total amount used per 100 parts by weight of N-(2-cyano-3-methylbutanoyl)urea: 25 parts by weight) to the reaction mixture. As a result, it took 18 hours to complete the hydrogen absorption.

The obtained reaction mixture was heated at 15–30° C. for 2 hours, and a solution of sodium hydroxide (70 g) in water (175 g) was added to the reaction mixture to filter off 10% palladium carbon. The filtrate was added dropwise to 35% hydrochloric acid (150 ml) at 20–30° C. to allow precipitation of the objective compound. The reaction mixture was filtered through a Nutsche funnel (time necessary for filtration: 30 minutes), and the obtained crystals were washed with water and dried to give 75.3 g of 5-isopropyluracil yield: 83%, purity: 99.55%.

From the foregoing results, it is apparent that the method of the present invention enables production of highly pure 5-isopropyluracil at a high yield in a short time.

This application is based on application Nos. 290161/1997 and 261942/1998 filed in Japan, the contents of which are incorporated hereinto by reference.

What is claimed is:

1. A method for producing 5-isopropyluracil, which comprises reducing N-(2-cyano-3-methylbutanoyl)urea in a 10–15% aqueous sulfuric acid solution in the presence of palladium carbon.

2. The production method of claim 1, wherein the reduction is carried out at 30–45° C.

3. The production method of claim 1, wherein the reduction is carried out at 30–40° C.

4. The production method of claim 1, wherein the reduction is carried out at 35–45° C.

5. The production method of claim 1, wherein the reaction mixture after reduction is heated and added to a 50–70% aqueous sulfuric acid solution to allow precipitation of 5-isopropyluracil.

* * * * *

UNITED STATES PATENT AND TRADEMARK OFFICE
CERTIFICATE OF CORRECTION

PATENT NO. : 5,914,399
DATED : June 22, 1999
INVENTOR(S) : Ueno et al.

It is certified that error appears in the above-indentified patent and that said Letters Patent is hereby corrected as shown below:

On the title page:

Under [56] References Cited, Line 3: "2,413,303" should read --2,443,303--, and "6/1946" should read --6/1948--.

Column 3, Line 6: "kg/cm" should read --kg/cm²--.

Column 4, Line 5: "mire" should read --mixture--.

Column 4, Line 22: "mire" should read --mixture--.

Column 6, Line 9: "yield" should read --(yield--.

Column 7, Line 12: "yield" should read --(yield--.

Column 7, Line 12: "99.55%" should read --99.55%)--.

Signed and Sealed this

Twenty-third Day of November, 1999

Attest:

Attesting Officer

Q. TODD DICKINSON

Acting Commissioner of Patents and Trademarks